United States Patent [19]

Barlow

[11] Patent Number: 4,761,511

[45] Date of Patent: Aug. 2, 1988

[54] CRYSTALLINE GALLOALUMINOSILICATES, STEAM-MODIFIED CRYSTALLINE GALLOALUMINOSILICATES, THEIR PREPARATION AND THEIR USE AS CATALYSTS AND CATALYST SUPPORTS

[75] Inventor: Michael T. Barlow, Byfleet, United Kingdom

[73] Assignee: BP Chemicals Limited, United Kingdom

[21] Appl. No.: 53,522

[22] Filed: May 19, 1987

Related U.S. Application Data

[60] Continuation of Ser. No. 908,952, Sep. 17, 1986, abandoned, which is a continuation of Ser. No. 757,184, Jul. 19, 1985, abandoned, which is a division of Ser. No. 593,613, Mar. 26, 1984, abandoned.

[30] Foreign Application Priority Data

Mar. 29, 1983 [GB] United Kingdom ............... 8308684

[51] Int. Cl.$^4$ ................................................ C07C 2/00
[52] U.S. Cl. .................................. 585/415; 585/417; 585/418; 585/520
[58] Field of Search ............... 585/415, 417, 418, 407, 585/520, 314, 315, 316, 329; 502/61

[56] References Cited

U.S. PATENT DOCUMENTS

| | | | |
|---|---|---|---|
| 3,843,741 | 10/1974 | Yan | 585/415 |
| 3,845,150 | 10/1974 | Yan et al. | 585/415 |
| 4,326,994 | 4/1982 | Haag et al. | 502/61 |
| 4,334,114 | 6/1982 | Ellis | 585/407 |
| 4,350,035 | 9/1982 | Chester et al. | 585/415 |
| 4,582,949 | 4/1986 | Kieffer | 585/415 |
| 4,704,494 | 11/1987 | Inui | 585/415 |
| 4,711,970 | 12/1987 | Cheng et al. | 585/415 |

*Primary Examiner*—Asok Pal
*Attorney, Agent, or Firm*—Brooks Haidt Haffner & Delahunty

[57] ABSTRACT

The invention relates to crystalline galloaluminosilicates having an X-ray diffraction pattern substantially the same as that of an MFI-zeolite and a composition in terms of mole ratios of oxides as follows:

$$0.9 \pm 0.2 \; M_{2/n}O \cdot Al_2O_3 \cdot a \; Ga_2O_3 \cdot b \; SiO_2 \cdot zH_2O$$

wherein M is a cation, n is the valence of the cation, a has a value between 0.0001 and 2, b has a value of at least 12 and z has a value of from 0 to 40. Ion-exchanged forms, calcined forms and steam-treated forms of the crystalline galloaluminosilicates are also described. Such materials can be used as catalysts and catalyst supports. The steam-treated form is particularly useful as a catalyst for the production of aromatic hydrocarbons from $C_2$ to $C_{12}$ hydrocarbon feedstocks.

11 Claims, 4 Drawing Sheets

FIG.4 CATALYST D.

CRYSTALLINE GALLOALUMINOSILICATES, STEAM-MODIFIED CRYSTALLINE GALLOALUMINOSILICATES, THEIR PREPARATION AND THEIR USE AS CATALYSTS AND CATALYST SUPPORTS

This application is a continutation, of application Ser. No. 06/908,952 filed Sept. 17, 1986, which is a continuation of application Ser. No. 06/757,184, filed July 19, 1985, which is a division of application Ser. No. 06/593,613 filed Mar. 26, 1984, now all abandoned.

The present invention relates to crystalline galloaluminosilicates, steam-modified crystalline galloaluminosilicates, their preparation and their use as catalysts and catalyst supports.

U.S. Pat. No. 3,702,886 (Mobil Oil Corporation) describes a novel family of ultra-stable synthetic siliceous crystalline materials designated as "Zeolite ZSM-5" or simply "ZSM-5" having a characteristic X-ray diffraction pattern and a composition in terms of mole ratios of oxides as follows:

$$0.9 \pm 0.2 M_{2/n}O : W_2O_3 : 5\text{-}100 YO_2 : zH_2O$$

wherein M is a cation, n is the valence of said cation, W is selected from the group consisting of aluminium and gallium, Y is selected from the group consisting of silicon and germanium, and z is from 0 to 40. Crystalline aluminosilicates having the aforesaid composition and characteristic X-ray diffraction pattern are classified in the Atlas of Zeolite Structure Types by W. M. Meier and D. H. Olson, published by the Structure Commission of the International Zeolite Association, 1978, as MFI-type zeolites. This patent was the forerunner to a vast number of patents relating to novel synthetic crystalline aluminosilicate zeolites all of which are charaterised by a high, that is 10:1 or greater, silica to alumina molar ratio, high stability, extremely high acidity and the ability to catalyse many kinds of conversion reactions, such as cracking, isomerisation of n-paraffins and naphthenes, polymerisation of olefinic and acetylenic compounds, reforming, alkylation, isomerisation of polyalkyl substituted aromatics and disproportionation.

The patent was also the forerunner of a number of patent publications relating to crystalline silicates. Examples of such patents include U.S. Pat. No. Re. 29,948; GB-A- No. 2023562; GB-A- No. 2024790; GB-A- No. 2033358 and GB-A- No. 2071071.

U.S. Pat. No. Re. 29,948 describes crystalline organosilicates having an MFI-type XRD pattern and a composition in the anhydrous state in terms of mole ratios of oxides as follows: $0.9 \pm 0.2[xR_2O + (1-x)M_{2/n}O]$: less than 0.005 Al$_2$O$_3$:greater than 1 SiO$_2$ where M is a metal other than a metal of Group 111A, i.e. not B, Al, Ga, In or Tl, n is the valence of said metal, R is an alkyl ammonium radical, and x is greater than 0 but not exceeding 1.

GB-A- No. 2023562 describes a zeolite having an X-ray diffraction spectrum akin to that of zeolite ZSM-5 and having the general formula:

$$(0.9 \pm 0.2)M_{2/n}O : W_2O_3 : (5\text{-}100)YO_2 : zH_2O$$

wherein M is a cation selected from H$_+$ and/or NH$_4$+ and/or metallic cations and/or cations deriving from amino alcohols (especially ethanolamines), n is the valency of the cation, W is aluminium or gallium, Y is silicon or germanium and z is from 0 to 40.

GB-A- No. 2024790 describes a modified silica characterised by the presence of a single crystalline phase and having the formula:

$$(0.0001 \text{ to } 1)M_nO_m \cdot SiO_2$$

wherein M$_n$O$_m$ is an oxide of the modifying element, which is preferably an element having, at least partially, an amphoteric character, e.g. Cr, Be, Ti, V, Mn, Fe, Co, Zn, Zr, Rh, Ag, Sn, Sb or B.

In GB-A- No. 2071071 there is described a porous crystalline synthetic material having the formula:

$$xTiO_2(1-x)SiO_2$$

wherein x is from 0.0005 to 0.04, and having a silicalite-type structure wherein the titanium substitutes for silicon.

Finally, GB-A- No. 2033358 describes an anhydrous composition having an XRD pattern characteristic of ZSM-5 zeolites and a composition, in terms of mole ratios of oxides as follows:

$$[R_2O, M_{2/n}{}^1O]W \cdot [Al_2O_3]_X \cdot [SiO_2]_y \cdot [M^{11}{}_{2/n}O]_z$$

wherein W/X is from greater than 0.5 to less than 3, Y/X is greater than 20 and Z/X is from zero to less than about 100, R is a nitrogen containing cation.

None of the foregoing patent publications specifically describe a crystalline galloaluminosilicate.

Finally, the deleterious effect of steam on zeolites has been recognised in the art. See, for example, U.S. Pat. No. 4,231,899 which contains the statement at column 1, lines 18 to 22:-

> The deleterious effect of steam on zeolites has been the subject of numerous papers and patents. This irreversible damage and loss of catalytic activity is thought to occur from hydrolysis of tetrahedral aluminium from the framework of the zeolite.

We have now prepared crystalline galloaluminosilicates having an XRD pattern substantially the same as an MFI-type zeolite. Although such materials have utility as catalysts and catalyst supports, particularly in hydrocarbon conversion processes, contrary to the teaching of the prior art with regard to aluminosilicates, steam treatment of crystalline galloaluminosilicates can improve their catalytic performance.

Accordingly, the present invention provides a crystalline galloaluminosilicate having an X-ray diffraction pattern substantially the same as that of an MFI-type zeolite and a composition in terms of mole ratios of oxides as follows:

$$0.9 \pm 0.2 M_{2/n}O \cdot Al_2O_3 \cdot a\ Ga_2O_3 \cdot b\ SiO_2 \cdot zH_2O$$

wherein M is a cation, n is the valence of the cation, a has a value between 0.0001 and 2, b has a value of at least 12 and z has a value of from 0 to 40.

The cation M may suitably be H+, NH$_4$+, a metallic cation or an organic nitrogen cation or a mixture of at least two such cations.

The aforesaid crystalline galloaluminiosilicate may suitably be prepared by crystallisation at elevated temperature from a gel comprising (i) a source of silica (SiO$_2$), (ii) a source of alumina (Al$_2$O$_3$), (iii) a source of gallia (Ga$_2$O$_3$), (iv) a mineralising agent selected from oxides, hydroxides and salts of alkali and alkaline earth metals (X$_{2/n}$O wherein n is the valence of X), (v) an organic base (B) and (vi) ROH wherein R is H and/or lower alkyl, in the following molar proportions:

SiO$_2$:M$_2^1$O$_3$ (wherein M$_2^2$O$_3$ is defined as total molar Al$_2$O$_3$+Ga$_2$O$_3$) greater than 12:1, preferably in the range 15:1 to 100:1,
SiO$_2$:X$_{2/n}$O=1000:1 to 50:1
SiO$_2$:B=50:1 to 1:20
SiO$_2$:ROH less than 1:10
Al$_2$O$_3$:Ga$_2$O$_3$=500:1 to 1:100, preferably 200:1 to 1:50.

The term organic base as used hereinbefore means any organic material (B) for which $-\log_{10}[K_D$ for the reaction:

$$B+H_2O \rightleftharpoons BH^+ + OH^-$$

is less than 7, where $K_D = [BH^+][OH^-]/[B]$.

Suitable organic bases include:
(i) tetraalkylammonium salts of the formula:

$$R^1R^2R^3R^4N^+X^-$$

wherein R$^1$, R$^2$, R$^3$ and R$^4$ are independently either aryl, substituted aryl, alkyl, substituted alkyl, cycloalkyl, substituted cycloalkyl or hydrogen and X$^-$ is either an inorganic or an organic anion. Preferably R$^1$, R$^2$, R$^3$ and R$^4$ are alkyl groups containing from 1 to 5 carbon atoms. Preferably X$^-$ is a halide or hydroxide ion. Suitable tetraalkylammonium salts include tetraethylammonium hydroxide and tetrapropylammonium hydroxide. Alternatively, the precursors of tetraalkylammonium compounds may be used.

(ii) amines having the formula: either R$^1$R$^2$R$^3$N, or R$^1$R$^2$N(CH$_2$)$_x$NR$^3$R$^4$ wherein x is an integer in the range 1 to 10, or R$^1$R$^2$N(CH$_2$)$_y$N(CH$_2$)$_z$NR$^3$R$^4$ wherein y and z are integers in the range 1 to 10. Suitable amines include C$_1$ to C$_9$ primary monoalkylamines, such as ethylamine, n-propylamine and n-butylamine.

(iii) Mono-, di- and tri-alkanolamines such as mono-ethanolamine, diethanolamine or triethanolamine, or their precursors in the form of an alkylene oxide and ammonia, eg ethylene oxide and ammonia, or mixtures thereof.

Suitable sources of gallia include gallium salts, alkali metal gallates and gallium oxide.

Suitable sources of silica include, for example, sodium silicate, silica hydrosol, silica gel, silica sol and silicic acid. The preferred source of silica is an aqueous colloidal dispersion of silica particles. A suitable commercially available source of silica is LUDOX (Registered Trade Mark) Colloidal Silica manufactured by DuPont.

Suitable sources of alumina include, for example, sodium aluminate, aluminium sulphate and alumina. The preferred source of alumina is sodium aluminate prepared by dissolving particulate alamina in excess sodium hydroxide solution.

The preferred mineralising agents are alkali and alkaline earth metal hydroxides and halides, such as for example, lithium hydroxide, sodium hydroxide, potassium hydroxide, potassium bromide and calcium bromide. The preferred mineralising agent is sodium hydroxide.

It will be appreciated that each source of silica, alumina, alkali or alkaline earth metal can be supplied by one or more initial reactants and then mixed together in any order. For example, sodium silicate is a source of both alumina and silica and an aluminosilicate is a source of both alumina and silica. Thus, the source of alumina and the source of silica may be supplied in whole or in part by an aluminosilicate, which may be either crystalline or amorphous, for example a clay such as bentonite or montmorillonite or an acid-leached clay.

The crystallisation temperature may suitably be in the range from 80° to 220° C., preferably from 120° to 175° C. The crystallisation pressure may suitably be autogenous pressure, that is the pressure generated within a closed vessel at the crystallisation temperature employed.

The gel may suitably be held under crystallisation conditions for a time greater than 0.5 hours and up to 150 hours.

As crystallised from such a gel, the crystalline galloaluminosilicate will almost certainly contain alkali or alkaline earth metal ions and possibly also organic nitrogen cations.

These original cations can be replaced in accordance with techniques well known in the art, at last in part by ion-exchange with other cations. Preferred replacing cations include ammonium ions, hydrogen ions and metal cations. Particularly preferred cations are those which enhance the galloaluminosilicate's catalytic activity, especially with regard to conversion reactions. These include hydrogen, rare earth metals, aluminium, gallium and metals of Group VIII of the Periodic Table. It is preferred, before exchange, and optionally between exchanges or after exchange, to calcine the crystalline galloaluminosilicate, i.e. to reduce the value of z in the aforesaid compositional formula to zero. Calcination may be effected by heating, suitably in a stream of dry air, at a temperature in the range from 400° to 600° C. for at least 0.5 hour. Replacement of exchangeable cations may be effected by conventional ion-exchange techniques.

In a preferred embodiment, the organic base in the aforedescribed galloaluminosilicate preparation may be replaced by a source of ammonium ions, such as for example an aqueous ammonia solution. An advantage of using a source of ammonium ions is that a calcination step prior to ion-exchange can be avoided if so-desired.

Alternatively, crystalline galloaluminosilicates may be produced by substituting a proportion of the alumina source by a gallia source in the processes described in for example U.S. Pat. Nos 3,775,501; 3,702,886 and 3,709,979 and GB Patents Nos. 1334243, 1365317, 1365318, 1553209 and 1567948 and UK application publication No. 2018232A.

In a modification of the present invention there is provided the crystalline galloaluminosilicate as hereinbefore described substantially in the hydrogen-form or the ammonium-form and modified by treatment with steam.

Surprisingly, in view of the teaching of U.S. Pat. No. 4,231,899 with regard to aluminosilicates, steam-modified hydrogen- or ammonium-exchanged galloaluminosilicates are better catalysts than their unsteamed counterparts for certain reactions, for example the aromatisation of hydrocarbons.

BRIEF DESCRIPTION OF THE DRAWINGS

FIGS. 1 through 4 illustrate graphically the unexpected improvements obtainable by the practice of the present invention.

In another aspect therefore the invention provides a process for the production of a steam-modified galloaluminosilicate which process comprises heating the hereinbefore described crystalline galloaluminosilicate substantially in the hydrogen-form or the ammonium-form with steam at a temperature in the range from 400° to 700° C. for a period of at least 0.5 hour.

The steam-modified galloaluminosilicate may, if desired, be further modified by ion-exchange with catalytically desirable metal cations, for example cations of metals of Group VIII of the Periodic Table.

The treatment with steam is effected for at least 0.5 hour and suitably for as long as 12 hours, though longer periods may be used if so desired. The steam may be neat steam or admixed with inert gases such as air, nitrogen or helium.

Whilst we do not wish to be bound in any way as to the mechanistic effects of steam treatment, it is believed that the treatment causes gallium to be preferentially removed from the framework of the crystalline galloaluminosilicate and deposited, probably in the form of gallium oxide, on the surface and in the pores thereof.

Both crystalline galloaluminosilicates and steam-modified galloaluminosilicates may be used as catalysts and catalyst supports in, for example, the conversion of synthesis gas to hydrocarbons and/or oxygenated derivatives thereof and the conversion of hydrocarbons to aromatic hydrocarbons. In particular, the steam-modified galloaluminosilicates are useful as catalysts in the dehydrocyclooligomerisation of hydrocarbons to condensable hydrocarbon fractions containing mononuclear aromatics such as benzene, toluene and xylene.

Accordingly, the present invention in another aspect provides a process for the production of aromatic hydrocarbons which process comprises contacting in the vapour phase a $C_2$ to $C_{12}$ hydrocarbon feedstock at elevated temperature with the steam-modified crystalline galloaluminosilicate as hereinbefore described.

By $C_2$ to $C_{12}$ hydrocarbon feedstock is meant a feedstock containing either a single hydrocarbon component or a mixture of saturated and/or unsaturated $C_2$ to $C_{12}$ hydrocarbons. The feedstock is suitably one or more saturated and/or unsaturated $C_2$ to $C_8$ hydrocarbons. Hydrocarbon feedstocks containing either ethane and/or ethylene, or propane and/or propylene, or isobutane and/or isobutane are particularly useful in the process of the invention.

The hydrocarbon feedstock may be contacted with the catalyst at a temperature suitably in the range from 400° to 700° C., preferably from 500° to 600° C.

Further details relating to process conditions may be found in, for example, GB No. 1561590 and European patent publication No. 50021 (BP Case No 5012), to which the reader is referred.

The invention will now be illustrated by reference to the following Examples.

A. PREPARATION OF CRYSTALLINE GALLOALUMINOSILICATES

EXAMPLE 1

Crystalline galloaluminosilicate (a)

1.08g of sodium hydroxide and 1.31g of sodium aluminate were dissolved in 35.6g of water. 1.25g of gallium nitrate were then added and the mixture stirred for 15 minutes. A second solution was made by adding 4.84g of 0.91 SG aqueous ammonia (ca 25% by wt $NH_3$) to 37.5g of Ludox AS40 colloidal silica. After the 25 minutes had elapsed, the second solution was added to the first with vigorous stirring over ca 5 minutes. At the end of this time the mixture was stirred for a further 5 minutes until the gel formed a uniform white paste.

The gel was transferred to a stainless steel 200 ml pressure vessel, the vessel sealed, and the mixture heated to 170° C. with slow agitation. After 72 hours at this temperature, the vessel was cooled and opened. The solid contents of the vessel were separated by filtration and washed with distilled water. The X-ray pattern of the solid product after drying was identical with that of an MFI zeolite.

EXAMPLE 2 TO 4

Crystalline galloaluminosilicates (b)–(d)

The method described in Example 1 of preparing galloaluminosilicate (a) was used but for each experiment the weights of materials used were those given in Table 1. In each case the solid product recovered after 72 hours crystallisation at 170° C. was identical with that of an MFI-type zeolite.

TABLE 1

| Ex | Galloalumino-silicate | Ludox AS40 | $H_2O$ | NaOH | $NaAlO_2$ | $Ga(NO_3)_3$ | $NH_3$ | Product |
|---|---|---|---|---|---|---|---|---|
| 2 | (b) | 37.5 | 35.6 | 1.25 | 1.31 | 1.25 | 1.04 | MFI-type zeolite |
| 3 | (c) | 37.5 | 35.6 | 0.7 | 1.31 | 1.25 | 3.4 | MFI-type zeolite |
| 4 | (d) | 37.5 | 35.6 | 0.9 | 1.31 | 1.25 | 6.5 | MFI-type zeolite |

The products obtained from these four preparations indicate that mixed galloaluminosilicates can be produced using aqueous ammonia over a range of chemical conditions.

EXAMPLE 5

Crystalline galloaluminosilicate (e)

6,000 g of Ludox AS40 colloidal silica (40% by wt $SiO_2$) was mixed with 2,030 g of a 20% by weight solution of tetrapropylammonium hydroxide. A second mixture consisting of a solution of 255 g of sodium aluminate (ca 40% $Al_2O_3$ by weight), 103.8 g of gallium nitrate and 48 g of sodium hydroxide in 4,072 g of water was prepared. The two solutions were mixed and stirred vigorously for 30 minutes.

The mixture was transferred to a 4 gallon autoclave and heated to 170° C. with stirring. After 72 hours the mixture was cooled and the solid product isolated by filtration. X-ray diffraction showed that the solid product had a powder pattern similar to ZSM-5. Analysis of the product revealed a $SiO_2$:$Al_2O_3$ ratio of 33.9 and a % wt gallium content of 0.74.

B. PREPARATION OF CATALYSTS DERIVED FROM GALLOALUMINOSILICATES

EXAMPLE 6

A sample of the MFI-galloaluminosilicate (a) (Example 1) was converted to the ammonium form by ion-exchange (twice) with 1M ammonium chloride solution for 2 hours at 100° C. The ammonium exchanged form of the product was carefully dried at 200° C. and then heated to 500° C. in dry air over a period of two hours. The catalyst was then heated for a further 18 hours at 500° C. in dry air. The catalyst will hereinafter be referrred to as Catalyst A.

EXAMPLE 7

The procedure of Example 6 was followed using MFI-galloaluminosilicate (a) (Example 1). However, on reaching 500° C. dry air was replaced for 2 hours by a feed consisting of 20% steam in air. Using this steam treatment the catalyst was further heated to 550° C. After 2 hours had elapsed the steamed catalyst was cooled to 500° C. and calcined for a further 18 hours in dry air. The catalyst will hereinafter be referred to as Catalyst B.

EXAMPLE 8

The MFI-galloaluminosilicate (b) (Example 2) was treated in identical manner to the MFI-galloaluminosilicate (a), as described in Example 6. The catalyst will hereinafter be referred to as Catalyst E.

EXAMPLE 9

The procedure of Example 7 was used except that MFI-galloaluminosilicate (b) was used in place of MFI-galloaluminosilicate (a). The catalyst will hereinafter be referred to as Catalyst F.

EXAMPLE 10

A sample of the MFI-galloaluminosilicate (e) obtained in Example 5 was calcined at 500° C. in dry air for 60 hours and then converted to the ammonium form by ion-exchange (twice) with 1M ammonium chloride solution for 2 hours at 100° C. The product was calcined in dry air at 500° C., followed by calcination in air containing 20% steam at 550° C. for 2 hours.

The catalyst will hereinafter be referred to as Catalyst G.

C. PREPARATION OF CATALYSTS DERIVED FROM MFI-TYPE ALUMINOSILICATES

Comparison Test 1

The method used to prepare Catalyst A was followed, but in place of the MFI galloaluminosilicate an MFI-type aluminosilicate was used (prepared by the method described in Example 1 of our European patent publication No. 30811). The catalyst was calcined for 18 hours in dry air at 500° C. The catalyst will hereinafter be referred to as Catalyst C.

Comparison Test 2

A sample of Catalyst C was steamed using the method described in Example 7. After 2 hours at 550° C. in a feed of 20% steam in air, the catalyst was cooled to 500° C. and calcined in dry air for 18 hours. The catalyst will hereinafter be referred to as Catalyst D.

Comparison Tests 1 and 2 are not Examples according to the invention and are included only for the purpose of comparison.

D. TESTING OF CATALYSTS

EXAMPLES 11 and 12

Catalysts A and B were tested individually in isothermal reactors for the conversion of propane into aromatics. The conditions used in each case were identical and were as follows:

Reaction Temperature = 535° C.
Contact Time = 6 secs (NTP)
Feed = Propane
Duration of Test = 6 hours
Pressure = 1 Atm

Comparison Tests 3 and 4

The procedure of Examples 11 and 12 was repeated using Catalysts C and D respectively in place of Catalysts A and B.

Figure 1:
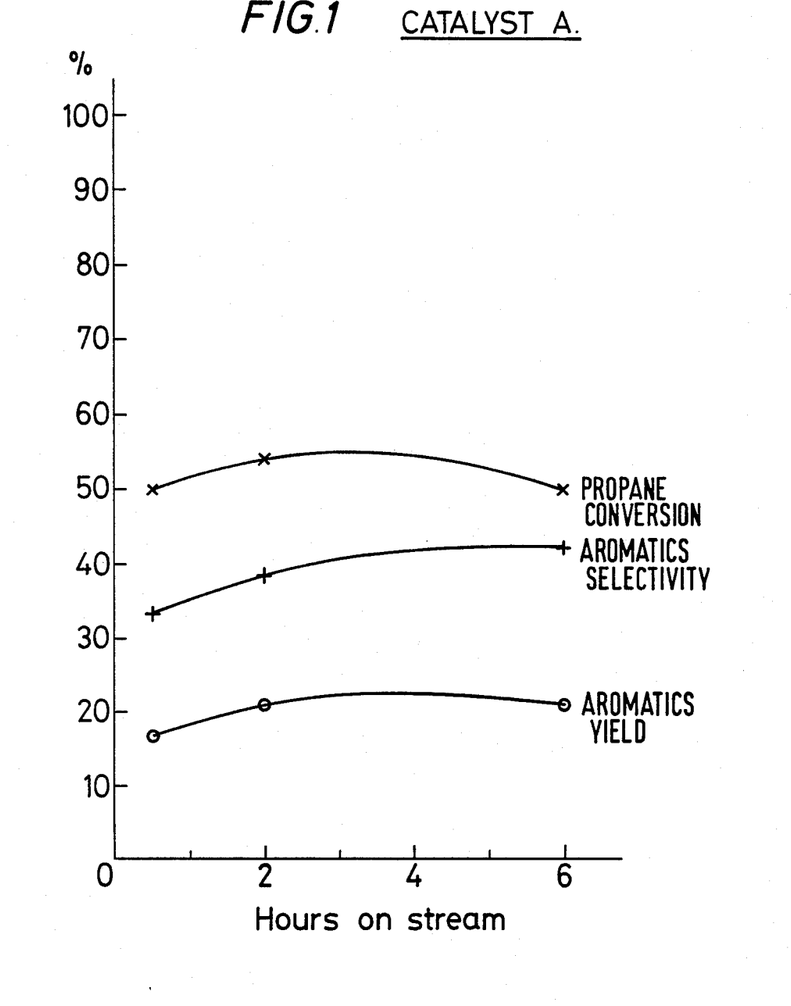
FIG. 1 plots the activity over time of an unsteamed galloaluminosilicate catalyst in the aromatization of propane.
Figure 2:
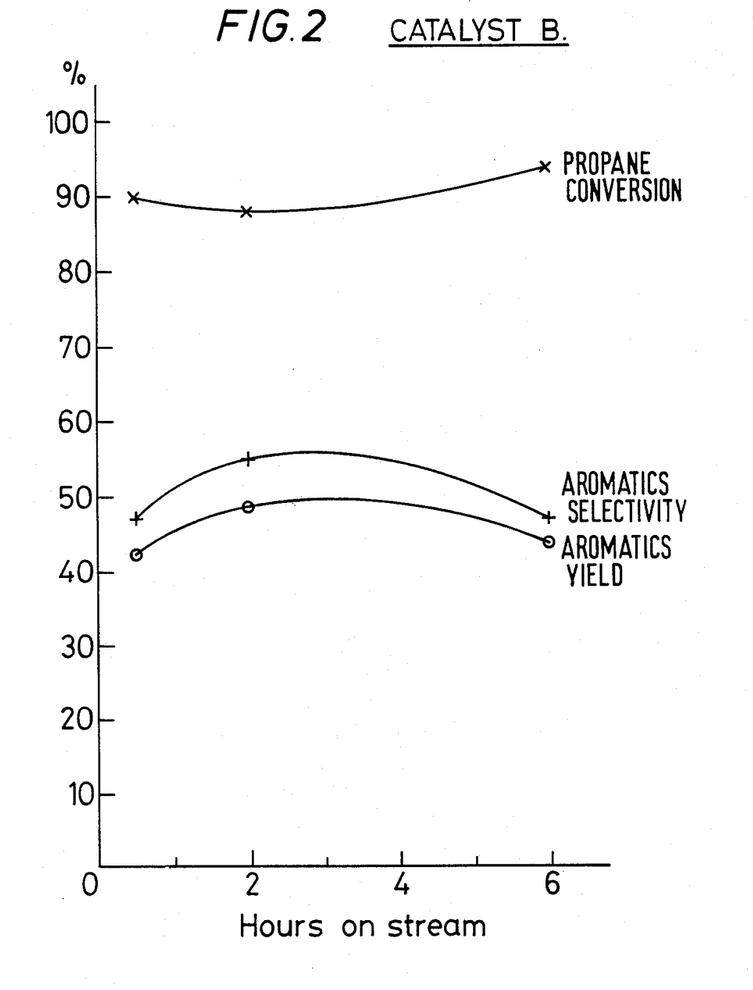
FIG. 2 plots the activity over time of a steamed galloaluminosilicate in accordance with the invention in the aromatization and conversion of propane. Similarly, FIGS. 3 and 4 compare the activity of a steamed (FIG. 4) and unsteamed (FIG. 3) MFI-aluminosilicate.
Figure 3:
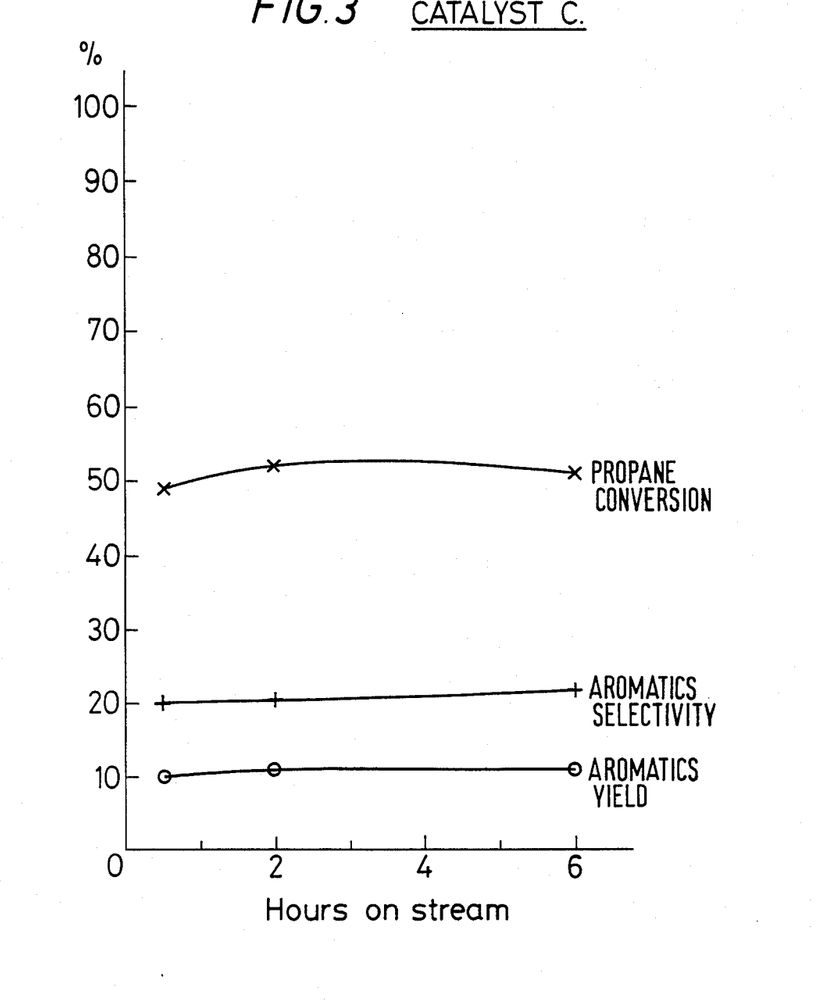
Figure 4:
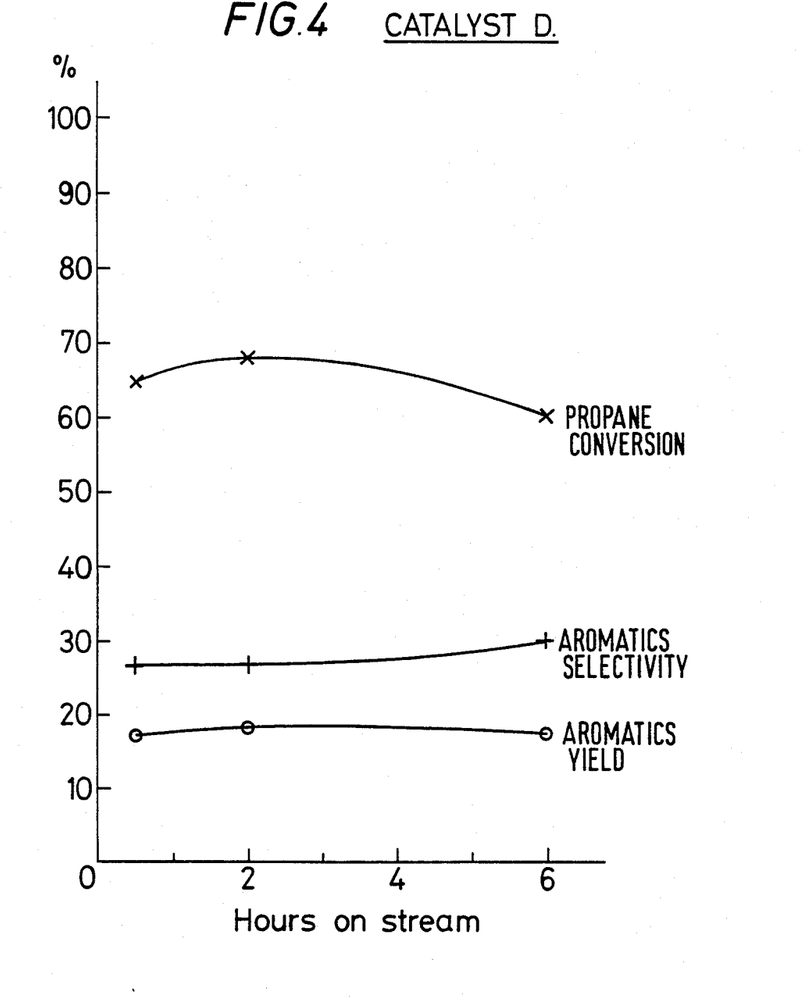

The results of Examples 11 and 12 and Comparison Tests 3 and 4 are illustrated graphically in FIGS. 1 to 4 which are as follows:

FIG. 1 (Example 11) - Catalyst A of Example 6.
FIG. 2 (Example 12) - Catalyst B of Example 7.
FIG. 3 (Comparative Test 3) - Catalyst C of Comparison Test 1.
FIG. 4 (Comparative Test 4) - Catalyst D of Comparison Test 2.

The results shown in FIGS. 1 to 4 clearly demonstrate the advantages of using a steamed galloaluminosilicate as catalyst in the conversion of propane to aromatics. The activity of the steamed galloaluminosilicate (FIG. 2) is very much higher than the unsteamed galloaluminosilicate (FIG. 1) and both the steamed and unsteamed MFI-aluminosilicates in the hydrogen form (FIGS. 3 and 4). Furthermore, the selectivity to aromatics (47 to 55%) for the steamed galloaluminosilicate (FIG. 2) is higher than for the unsteamed galloaluminosilicate (FIG. 1) which in turn is higher than the MFI-aluminosilicates (FIGS. 3 and 4) and is in fact similar to that obtained for a gallium impregnated and/or exchanged aluminosilicate.

EXAMPLE 13 and 14

The procedure of Examples 11 and 12 was repeated except that Catalysts A and B were replaced by Catalysts E and F respectively. The results are given in Table 2.

TABLE 2

| | HOURS ON STREAM | | | | | | | |
|---|---|---|---|---|---|---|---|---|
| | 0.5 | | 2 | | 4 | | 6 | |
| Example | $C_3H_8$ Conversion (%) | $S_A$* | $C_3H_8$ Conversion (%) | $S_A$* | $C_3H_8$ Conversion (%) | $S_A$* | $C_3H_8$ Conversion (%) | $S_A$* |
| 13 | 55 | 13.7 | 53 | 21.9 | 49 | 20.2 | 49 | 17.9 |
| 14 | 86 | 46.2 | 84 | 42.6 | 81 | 52.0 | 77 | 48.4 |

*$S_A$ = % by wt selectivity to aromatics.

The results in Table 2 demonstrate that steaming the crystalline galloaluminosilicate improves both the activity and the selectivity of the material as a catalyst in the DHCD of propane to aromatics.

EXAMPLE 15

Catalyst G of Example 10 was activated for 4 hours in dry air at 550° C.

The activated catalyst was the tested for DHCD of butane under the following conditions:-
Temperature=540° C.
Contact time=16 secs (NTP)
Feed=butane
Pressure=6 Atm
Duration of test=93 hours
The results obtained are shown in Table 3.

TABLE 3

|  | HOS | | | | |
| --- | --- | --- | --- | --- | --- |
|  | 4 | 25 | 49 | 73 | 93 |
| % $C_4$ Conv. | 99.3 | 98.6 | 98.1 | 94.7 | 89.1 |
| % ($C_3$ + $C_4$) Conv. | 85.7 | 79.8 | 72.4 | 66.1 | 59.8 |
| % Aromatics | | | | | |
| Yield | 44.4 | 42.6 | 40.3 | 38.2 | 34.4 |
| Selectivity | 51.8 | 53.3 | 55.7 | 57.7 | 57.4 |

I claim:

1. A process for the production of aromatic hydrocarbons which process comprises contacting in the vapour phase a $C_2$ to $C_{12}$ hydrocarbon feedstock at elevated temperature with the steam-modified crystalline galloaluminosilicate in the hydrogen-form or ammonium-form, said crystalline galloaluminosilicate having an X-ray diffraction pattern substantially the same as that of an MFI-zeolite and a composition in terms of mole ratios of oxides as follows:

$$0.9 + 0.2 M_{2/n}O \cdot Al_2O_3 \cdot a\, Ga_2O_3 \cdot b\, SiO_2 \cdot zH_2O$$

wherein M is a cation, n is the valence of the cation, a has a value between 0.0001 and 2, b has a value of at least 12 and z has a value of from 0 to 40.

2. The process accroding to claim 1 wherein the cation M is $H^+$, $NH_4^+$, a metallic cation or an organic nitrogen cation or a mixture of at least two such cations.

3. The process according to claim 2, wherein the metallic cation is a cation of a rate earth metal, aluminium, gallium or a Group VIII metal.

4. The process according to claim 1, wherein z in the compositional formula is zero.

5. The process according to claim 1, wherein said crystalline galloaluminosilicate is produced by a process which comprises crystallising at elevated temperature a gel comprising (i) a source of silica ($SiO_2$), (ii) a source of alumina ($Al_2O_3$), (iii) a source of gallia ($Ga_2O_3$), (iv) a mineralising agent selected from oxides, hydroxides and salts of alkali and alkaline earth metals ($X_{2/n}O$ wherein n is the valency of X), (v) an organic base (B) and (vi) ROH wherein R is H and/or lower alkyl, in the following molar proportions:

$SiO_2:M_2^1O_3$ (wherein $M_2^{1I}O_3$ is defined as total molar $Al_2O_3 + Ga_2O_3$) = greater than 12:1,
$SiO_2:X_{2/n}O = 1000:1$ to $50:1$
$SiO_2:B = 50:1$ to $1:20$
$SiO_2:ROH = $ less than $1:10$,
$Al_2O_3:Ga_2O_3 = 500:1$ to $1:100$ 6. The process according to claim 5, wherein instead of the organic base (B) there is used a source of ammonium ions.

7. The process according to claim 1, wherein said steam-modified orystalline galloaluminosilicate is produced by a process which comprises heating said crystalline galloaluminosilicate substantially in the hydrogen-form or the ammonium form with steam at a temperature in the range from 400° to 700° C. for a period of at least 0.5 hour.

8. The process according to claim 1, wherein said steam-modified crystalline galloaluminosilicate is used as a catalyst or a catalyst support.

9. The process according to claim 1, wherein said hydrocarbon feedstock comprises propane.

10. The process according to claim 1, wherein said hydrocarbon feedstock comprises butane.

11. The process according to claim 1, wherein said hydrocarbon feedstock comprises propane and butane.

* * * * *

UNITED STATES PATENT AND TRADEMARK OFFICE
CERTIFICATE OF CORRECTION

PATENT NO. : 4,761,511

DATED : August 2, 1988

INVENTOR(S) : Michael T. Barlow

It is certified that error appears in the above-identified patent and that said Letters Patent is hereby corrected as shown below:

Col. 2, 1. 25, should read:

$$[R_2O, M^I_{2/n}O]W : [Al_2O_3]_X : [SiO_2]_Y : [M^{II}_{2/n}O]_Z$$

Col. 3, 1. 6, should read ...(wherein $M_2^IO_3$...

Col. 3, 1. 15, should read "$\log_{10}[K_D]$..."

Col. 3, 1. 57, should read "particulate al$\underline{u}$mina"

Claim 2, 1. 1, correct spelling of "according"

Claim 3, 1. 2, correct spelling of "rare"

Claim 5, 1. 11, should read ...(wherein $M_2^IO_3$ is...

Claim 7, 1. 2, correct the spelling of "crystalline"

Signed and Sealed this

Fourteenth Day of March, 1989

*Attest:*

DONALD J. QUIGG

*Attesting Officer*  *Commissioner of Patents and Trademarks*